(12) United States Patent
DeLuca et al.

(10) Patent No.: US 7,713,952 B2
(45) Date of Patent: May 11, 2010

(54) 2-METHYLENE-19,26,27-TRINOR-(20S)-1α-HYDROXYVITAMIN D3 AND ITS USES

(75) Inventors: Hector F. DeLuca, Deerfield, WI (US); Lori A. Plum, Arena, WI (US); Pawel K. Grzywacz, Madison, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/775,087

(22) Filed: Jul. 9, 2007

(65) Prior Publication Data

US 2007/0249567 A1  Oct. 25, 2007

Related U.S. Application Data

(63) Continuation of application No. 11/283,306, filed on Nov. 18, 2005, now Pat. No. 7,244,719.

(60) Provisional application No. 60/629,965, filed on Nov. 22, 2004.

(51) Int. Cl.
*A61K 31/59* (2006.01)
*C07C 401/00* (2006.01)

(52) U.S. Cl. ..................... 514/167; 552/653

(58) Field of Classification Search .................. 514/167; 552/653
See application file for complete search history.

(56) References Cited

U.S. PATENT DOCUMENTS

| | | | |
|---|---|---|---|
| 4,486,333 A * | 12/1984 | Sebba .................. | 516/14 |
| 4,666,634 A | 5/1987 | Miyamoto et al. | |
| 4,800,198 A | 1/1989 | DeLuca et al. | |
| 5,086,191 A | 2/1992 | DeLuca et al. | |
| 5,536,713 A | 7/1996 | Deluca et al. | |
| 5,578,587 A | 11/1996 | DeLuca et al. | |
| 5,585,369 A | 12/1996 | DeLuca et al. | |
| 5,587,497 A | 12/1996 | DeLuca et al. | |
| 5,843,928 A | 12/1998 | Deluca et al. | |
| 5,877,168 A | 3/1999 | Miyamoto et al. | |
| 5,936,133 A | 8/1999 | DeLuca et al. | |
| 5,945,410 A | 8/1999 | DeLuca et al. | |
| 6,127,559 A | 10/2000 | DeLuca et al. | |
| 6,392,071 B1 | 5/2002 | DeLuca et al. | |
| 6,537,981 B2 | 3/2003 | DeLuca et al. | |
| 6,753,013 B1 * | 6/2004 | Didriksen et al. ........... | 424/484 |
| 6,806,262 B2 | 10/2004 | DeLuca et al. | |
| 6,846,811 B2 | 1/2005 | DeLuca et al. | |
| 6,887,860 B2 | 5/2005 | DeLuca et al. | |
| 6,992,074 B2 | 1/2006 | DeLuca et al. | |
| 7,094,916 B2 | 8/2006 | DeLuca et al. | |
| 2004/0220418 A1 | 11/2004 | DeLuca et al. | |
| 2005/0119242 A1 | 6/2005 | DeLuca et al. | |
| 2005/0143358 A1 | 6/2005 | DeLuca et al. | |
| 2007/0249568 A1 | 10/2007 | DeLuca et al. | |
| 2007/0249569 A1 | 10/2007 | DeLuca et al. | |
| 2007/0254857 A1 | 11/2007 | DeLuca et al. | |
| 2007/0259838 A1 | 11/2007 | DeLuca et al. | |
| 2007/0270391 A1 | 11/2007 | DeLuca et al. | |

FOREIGN PATENT DOCUMENTS

| | | |
|---|---|---|
| WO | 2005051323 | 6/2005 |
| WO | 2005051396 | 6/2005 |

OTHER PUBLICATIONS

Kamycheva et al, "Intakes of Calcium and Vitamin D Predict Body Mass Index in the Population of Northern Norway," The Journal of Nutrition, 2002.
Arunabh et al, "Body Fat Content and 25-Hydroxyvitamin D Levels in Healthy Women," The Journal of Clinical Endocrinology & Metabolism, 88 (1): 157-161, 2003.

* cited by examiner

*Primary Examiner*—Sabiha Qazi
(74) *Attorney, Agent, or Firm*—Andrus, Sceales, Starke & Sawall, LLP (57) ABSTRACT

This invention discloses 2-methylene-19,26,27-trinor-(20S)-vitamin D analogs, and specifically 2-methylene-19,26,27-trinor-(20S)-1α-hydroxyvitamin $D_3$ and pharmaceutical uses therefor. This compound exhibits pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also has little, if any, calcemic activity and therefore may be used to treat autoimmune disorders or inflammatory diseases in humans as well as renal osteodystrophy. This compound may also be used for the treatment or prevention of obesity.

30 Claims, 6 Drawing Sheets

$K_i$: $1,25(OH)_2D_3 = 4.4 \times 10^{-11}$ M

OM (2-methylene-19,26,27-trinor-(20S)-1α-hydroxyvitamin $D_3$)= $7.7 \times 10^{-11}$ M

2-METHYLENE-19,26,27-TRINOR-(20S)-1α-HYDROXYVITAMIN D3 AND ITS USES

CROSS REFERENCE TO RELATED APPLICATION

This application is a continuation of U.S. patent application Ser. No. 11/283,306, filed Nov. 18, 2005, now U.S. Pat. No. 7,244,719.

This application claims priority to U.S. Provisional Application No. 60/629,965, filed Nov. 22, 2004.

BACKGROUND OF THE INVENTION

This invention relates to vitamin D compounds, and more particularly to 2-methylene-19,26,27-trinor-(20S)-1α-Hydroxyvitamin $D_3$ and its pharmaceutical uses.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

SUMMARY OF THE INVENTION

The present invention is directed toward 2-methylene-19,26,27-trinor-(20S)-vitamin D analogs, and more specifically toward 2-methylene-19,26,27-trinor-(20S)-1α-hydroxyvitamin $D_3$, their biological activity, and various pharmaceutical uses for these compounds.

Structurally these analogs are characterized by the general formula I shown below:

I where $X_1$ and $X_2$, which may be the same or different, are each selected from hydrogen or a hydroxy-protecting group. The preferred analog is 2-methylene-19,26,27-trinor-(20S)-1α-hydroxyvitamin $D_3$ which has the following formula Ia:

Ia

The above compounds of formula I, especially the compound of formula Ia, exhibit a desired, and highly advantageous, pattern of biological activity. These compounds are characterized by relatively high binding to vitamin D receptors, but very low intestinal calcium transport activity, as compared to that of 1α,25-dihydroxyvitamin $D_3$, and have very low ability to mobilize calcium from bone, as compared to 1α,25-dihydroxyvitamin $D_3$. Hence, these compounds can be characterized as having little, if any, calcemic activity. It is undesirable to raise serum calcium to supraphysiologic levels when suppressing the preproparathyroid hormone gene (Darwish & DeLuca, Arch. Biochem. Biophys. 365, 123-130, 1999) and parathyroid gland proliferation. These analogs having little or no calcemic activity while very active on differentiation are expected to be useful as a therapy for suppression of secondary hyperparathyroidism of renal osteodystrophy.

The compounds I, and particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity. Thus, these compounds also provide a therapeutic agent for the treatment of psoriasis, or as an anti-cancer agent, especially against leukemia, colon cancer, breast cancer, skin cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only result in moisturizing of skin but also improves the barrier function of skin.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat the above-noted diseases and disorders in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

FIGS. 1-6 illustrate various biological activities of 2-methylene-19,26,27-trinor-(20S)-1α-hydroxyvitamin $D_3$, hereinafter referred to as "OM," as compared to the native hormone 1α,25-dihydroxyvitamin $D_3$, hereinafter "$1,25(OH)_2D_3$."

DETAILED DESCRIPTION OF THE INVENTION 2-methylene-19,26,27-trinor-(20S)-1α-hydroxyvitamin $D_3$ (referred to herein as OM) was synthesized and tested. Structurally, this 19-nor analog and its pro-drug (in protected hydroxy form) is characterized by the general formula I previously illustrated herein, while the analog OM itself is represented by the formula Ia.

The preparation of 2-methylene-19,26,27-trinor-(20S)-1α-hydroxyvitamin $D_3$ having the structure Ia as well as compounds I can be accomplished by a common general method, i.e. the condensation of a bicyclic Windaus-Grundmann type ketone II with the allylic phosphine oxide III to the corresponding 2-methylene-19,26,27-trinor-vitamin D analog IV followed by deprotection at C-1 and C-3 in the latter compound:

IV

In the structures III and IV, groups $X_1$ and $X_2$ are hydroxy-protecting groups, preferably t-butyldimethylsilyl, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The hydrindanone of the general structure II is not known. It can be prepared by the method shown on Schemes 1 and 2 (see the preparation of compound OM).

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I and Ia is illustrated and described more completely in U.S. Pat. No. 5,843,928 entitled "2-Alkylidene-19-Nor-Vitamin D Compounds" the specification of which is specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

More specifically, reference should be made to the following description as well as to Schemes 1, 2 and 3 herein for a detailed illustration of the preparation of compound OM.

Preparation of (20S)-de-A,B-8β-(tert-butyldimethylsilyl)oxy-20-(hydroxymethyl)pregnane (2).

Ozone was passed through a solution of vitamin $D_2$ (3 g, 7.6 mmol) in methanol (250 mL) and pyridine (2.44 g, 2.5 mL, 31 mmol) for 50 min at −78° C. The reaction mixture was then flushed with an oxygen for 15 min to remove the residual ozone and the solution was treated with $NaBH_4$ (0.75 g, 20 mmol). After 20 min the second portion of $NaBH_4$ (0.75 g, 20 mmol) was added and the mixture was allowed to warm to room temperature. The third portion of $NaBH_4$ (0.75 g, 20 mmol) was then added and the reaction mixture was stirred for 18 h. The reaction was quenched with water (40 mL) and the solution was concentrated under reduced pressure. The residue was extracted with ethyl acetate (3×80 mL) and the combined organic phase washed with 1M aq. HCl, saturated aq. $NaHCO_3$, dried ($Na_2SO_4$) and concentrated under reduced pressure. The residue was chromatographed on silica gel with hexane/ethyl acetate (75:25) to give (20S)-de-A,B-20-(hydroxymethyl)pregnan-8β-ol 1 (1.21 g, 75% yield) as white crystals.

tert-Butyldimethylsilyl trifluoromethanesulfonate (3.24 mL, 3.72 g, 14.1 mmol) was added to a solution of the 8β,20-diol 1 (1 g, 4.7 mmol) and 2,6-lutidine (1.64 mL, 1.51 g, 14.1 mmol) in anhydrous DMF (15 mL) at 0° C. The mixture was stirred under argon at 0° C. for 1 h and then at room temperature for 18 h. The reaction was quenched with water (50 mL) and extracted with ethyl acetate (3×30 mL). The combined organic phase washed with brine, dried ($Na_2SO_4$) and concentrated under reduced pressure. The residue was dissolved in anhydrous THF (8 mL), triethylamine (3 mL, 2.17 g, 21.5 mmol) and a solution of tetrabutylammonium fluoride (1 M in THF, 6.5 mL, 6.5 mmol) were added, followed by freshly activated molecular sieves 4A (3 g). The reaction mixture was stirred under argon at room temperature for 4 h, then filtered through a short layer of Celite and evaporated. The residue was dissolved in ethyl acetate (30 mL), washed with brine, water, dried ($Na_2SO_4$) and concentrated under reduced pressure. The pure alcohol 2 (1.42 g, 93% yield) was isolated by a chromatography on silica gel with hexane/ethyl acetate (97.5:2.5→95:5), as a colorless oil: $^1$H NMR (500 MHz, $CDCl_3$) δ 4.00 (1H, d, J=2.4 Hz, 8α-H), 3.63 (1H, dd, J=10.5, 3.2 Hz, 22-H), 3.39 (1H, dd, J=10.5, 6.8 Hz, 22-H), 1.94 (1H, br.d, J=12.5 Hz), 1.02 (3H, d, J=6.6 Hz, 21-$H_3$), 0.924 (3H, s, 18-$H_3$), 0.882 (9H, s, Si-t-Bu), 0.005 and −0.010 (each 3H, each s, each Si—Me); $^{13}$C NMR (125 MHz) δ 69.29 (d, C-8), 67.94 (t, C-22), 53.06 (d), 52.80 (d), 42.12 (s, C-13), 40.54 (t), 38.27 (d), 34.39 (t), 26.79 (t), 25.79 (q, $SiCMe_3$), 23.08 (t), 18.00 (s, $SiCMe_3$), 17.61 (t), 16.65 (q, C-21), 13.75 (q, C-18), −4.81 and −5.18 (each q, each SiMe).

Preparation of (20S)-de-A,B-8β-(tert-butyldimethylsilyl)oxy-20-formylpregnane (3).

Sulfur trioxide pyridine complex (1.32 g, 8.28 mmol) was added to a solution of the alcohol 2 (451 mg, 1.38 mmol), triethylamine (960 µL, 697 mg, 6.9 mmol) in anhydrous methylene chloride (20 mL) and anhydrous DMSO (5 mL) at 0° C. The reaction mixture was stirred under argon at 0° C. for 20 min. and then concentrated. The residue was purified by column chromatography on silica gel with hexane/ethyl acetate (95:5) to give the aldehyde 3 (364 mg, 81% yield) as an oil: $^1$H NMR (500 MHz, CDCl$_3$) δ 9.55 (1H, d, J=3.1 Hz, CHO), 4.00 (1H, s, 8α-H), 2.33 (1H, m, 20-H), 1.89 (1H, dm, J=12.4 Hz), 1.07 (3H, d, J=6.8 Hz, 21-H$_3$), 0.939 (3H, s, 18-H$_3$), 0.862 (9H, s, Si-t-Bu), −0.009 and −0.026 (each 3H, each s, each SiMe); $^{13}$C NMR (125 MHz) δ 205.37 (d, CHO), 68.99 (d, C-8), 52.28 (d), 51.58 (d), 49.15 (d), 42.58 (s, C-13), 40.35 (t), 34.29 (t), 26.16 (t), 25.74 (q, SiCMe$_3$), 23.27 (t), 17.96 (s, SiCMe$_3$), 17.52 (t), 14.04 (q, C-21), 13.28 (q, C-18), −4.85 and −5.23 (each q, each SiMe).

Preparation of (20R)-de-A,B-8β-(tert-butyldimethylsilyl)oxy-20-(hydroxymethyl)pregnane (4).

The aldehyde 3 (364 mg, 1.12 mmol) was dissolved in methylene chloride (15 mL) and a 40% aq. n-Bu$_4$NOH solution (1.47 mL, 1.45 g, 2.24 mmol) was added. The resulting mixture was stirred under argon at room temperature for 16 h, diluted with methylene chloride (20 mL), washed with water, dried (Na$_2$SO$_4$) and concentrated under reduced pressure. A residue was chromatographed on silica gel with hexane/ethyl acetate (95:5) to afford a mixture of aldehyde 3 and its 20-epimer (292 mg, 80% yield) in ca. 1:2 ratio (by $^1$H NMR).

This mixture of aldehydes (292 mg, 0.9 mmol) was dissolved in THF (5 mL) and NaBH$_4$ (64 mg, 1.7 mmol) was added, followed by a dropwise addition of ethanol (5 mL). The reaction mixture was stirred at room temperature for 30 min and it was quenched with a saturated aq. NH$_4$Cl solution. The mixture was extracted with ether (3×20 mL) and the combined organic phase washed with water, dried (Na$_2$SO$_4$) and concentrated under reduced pressure. The residue was chromatographed on silica gel with hexane/ethyl acetate (96:4→80:20) to give the desired, pure (20R)-alcohol 4 (160 mg, 55% yield) as an oil and a mixture of 4 and its 20-epimer 2 (126 mg, 43% yield) in ca. 1:3 ratio (by $^1$H NMR).

4: $[α]_D$ +40.8° (c 1.09, CHCl$_3$); $^1$H NMR (500 MHz, CDCl$_3$) δ 4.00 (1H, d, J=1.9 Hz, 8α-H), 3.70 (1H, dd, J=10.6, 3.2 Hz, 22-H), 3.43 (1H, dd, J=10.6, 7.0 Hz, 22-H), 0.94 (3H, d, J=6.7 Hz, 21-H$_3$), 0.927 (3H, s, 18-H$_3$), 0.884 (9H, s, Si-t-Bu), 0.007 and −0.006 (each 3H, each s, SiMe$_2$); $^{13}$C NMR (125 MHz) δ 69.30 (d, C-8), 66.83 (t, C-22), 53.02 (d), 52.96 (d), 41.91 (s, C-13), 40.12 (t), 37.48 (d), 34.38 (t), 26.71 (t), 25.79 (q, SiCMe$_3$), 22.85 (t), 18.01 (s, SiCMe$_3$), 17.64 (t), 16.58 (q, C-21), 14.07 (q, C-18), 4.81 and −5.18 (each q, each SiMe).

Preparation of (20R)-de-A,B-8β-(tert-butyldimethylsilyl)oxy-20-(iodomethyl)pregnane (5).

A solution of iodine (471 mg, 1.84 mmol) in methylene chloride (30 mL) was slowly added to a solution of triphenylphosphine (482 mg, 1.84 mmol) and imidazole (250 mg, 3.68 mmol) in methylene chloride (15 mL) at 0° C. After 15 min. a solution of alcohol 4 (149 mg, 0.46 mmol) in methylene chloride (3 mL) was added into the mixture. After being stirring for 20 min. at 0° C., followed by 18 h at room temperature, the reaction mixture washed with water, dried (Na$_2$SO$_4$) and concentrated under reduced pressure. The residue was chromatographed on silica gel with hexane/ethyl acetate (97:3) to give the desired iodide 5 (201 mg, 100%): $[α]_D$ −0.3° (c 0.97, CHCl$_3$); $^1$H NMR (500 MHz, CDCl$_3$) δ 3.99 (1H, s, 8α-H), 3.46 (1H, dd, J=9.5, 2.9 Hz, 22-H), 3.18 (1H, dd, J=9.5, 6.4 Hz), 1.88-1.74 (3H, m), 1.67 (1H, dm, J=13.9 Hz), 0.95 (3H, d, J=6.4 Hz, 21-H$_3$), 0.918 (3H, s, 18-H$_3$), 0.882 (9H, s, Si-t-Bu), 0.008 and −0.008 (each, 3H, each s, SiMe$_2$); $^{13}$C NMR (125 MHz) δ 69.27 (d, C-8), 55.19 (d), 52.69 (d), 41.99: (s, C-13), 40.48 (t), 36.15 (d), 34.24 (t), 26.90 (t), 25.80 (q, SiCMe$_3$), 22.81 (t), 21.38 (q, C-21), 19.58 (t), 18.02 (s, SiCMe$_3$), 17.63 (t), 14.12 (q, C-18), −4.79 and −5.17 (each q, each SiMe); MS (EI) m/z 436 (15, M$^+$), 421 (8, M$^+$−CH$_3$), 393 (9, M$^+$−C$_3$H$_7$), 379 (98, M$^+$−t-Bu), 303 (65, M$^+$−t-BuMe$_2$SiOH−H), 177 (70), 135 (70), 95 (55), 75 (100); exact mass calculated for C$_{19}$H$_{37}$OSiI (M$^+$) 436.1658, found 436.1672.

Preparation of (20S)-de-A,B-8β-(tert-butyldimethylsilyl)oxy-20-(3-isopropoxycarbonyl)propyl-pregnane (6).

A mixture of zinc powder (124 mg, 1.9 mmol), anhydrous pyridine (4 mL) and isopropyl acrylate (235 µL, 217 mg, 1.9 mmol) was warmed to 50° C., then nickel(II) chloride hexahydrate (109 mg, 0.46 mmol) was added. The resulting mixture was warmed to 65° C. and stirred for 2 h until its green color turned to reddish brown one. After cooling to 0° C., a solution of iodide 5 (222 mg, 0.51 mmol) in anhydrous pyridine (3 mL) was added and the reaction mixture was stirred for 4 h at room temperature. The mixture was diluted with ethyl acetate (20 mL) and the resulting precipitate was filtered off through a pad of Celite. The filtrate washed with 5% aq. HCl and brine, dried (Na$_2$SO$_4$) and concentrated under reduced pressure. The residue was chromatographed on silica gel with hexane and hexane/ethyl acetate (95:5) to give the ester 6 (177 mg, 82%): $[α]_D$ +19.7° (c 1.13, CHCl$_3$); $^1$H NMR (400 MHz, CDCl$_3$) δ 5.00 (1H, sep, J=6.3 Hz, OCHMe$_2$), 3.99 (1H, d, J=2.2 Hz, 8α-H), 2.23 (1H, dd, J=7.4, 2.5 Hz, 24-H), 2.21 (1H, dd, J=6.8, 1.9 Hz, 24-H), 1.90 (1H, dm, J=12.2 Hz), 1.22 (6H, d, J=6.3 Hz, OCHMe$_2$), 0.895 (3H, s, 18-H$_3$), 0.881 (9H, s, Si-t-Bu), 0.82 (3H, d, J=6.6 Hz, 21-H$_3$), 0.001 and −0.012 (each, 3H, each s, SiMe$_2$); $^{13}$C NMR (100 MHz) δ 173.48 (s, COO-iPr), 69.45 (d, C-8), 67.31 (d, COOCHMe$_2$), 56.29 (d), 53.08 (d), 42.16 (s, C-13), 40.64 (t), 35.05 (t), 34.71 (t), 34.51 (d), 34.44 (t), 27.16 (t), 25.80 (q, SiCMe$_3$), 22.93 (t), 21.92 (t), 21.86 (q, COOCHMe$_2$), 18.48 (q, C-21), 18.02 (t), 17.69 (s, SiCMe$_3$), 14.01 (q, C-18), −4.79 and −5.16 (each q, each SiMe); MS (EI) m/z 424 (5, M$^+$), 409 (15, M$^+$−CH$_3$), 381 (35, M$^+$−C$_3$H$_7$), 367 (89, M$^+$−t-Bu), 321 (39, M$^+$−CH$_3$COOCHMe$_2$−H), 307 (85, M$^+$−CH$_3$CH$_2$COOCHMe$_2$−H), 283 (65), 265 (41), 249 (45), 233 (60), 215 (73), 189 (70), 163 (78), 135 (86), 109 (70), 95 (79), 75 (100); exact mass calculated for C$_{25}$H$_{48}$O$_3$Si (M$^+$) 424.3373, found 424.3371.

Preparation of (20S)-de-A,B-8β-(tert-butyldimethylsilyl)oxy-20-(4-hydroxy)butyl-pregnane (7)

Lithium aluminium hydride (20 mg, 0.53 mmol) was added to a solution of ester 6 (188 mg, 0.28 mmol) in anhydrous THF (5 mL) at 0° C. The reaction mixture was stirred for 30 min at 0° C., then a cooling bath was removed and the stirring was continued for additional 19 h at room temperature. The excess hydride was quenched by careful, successive addition of sat. aq. NH$_4$Cl. Methylene chloride (15 mL) and Celite (0.5 g) were added and the slurry was stirred for 20 min. The aluminium salts were separated by vacuum filtering the slurry through a Celite pad. The salts were repeatedly washed with methylene chloride. The filtrate was dried (Na$_2$SO$_4$) and concentrated under reduced pressure. A residue was chromatographed on silica gel with hexane/ethyl acetate (90:10) to afford the alcohol 7 (96 mg, 93% yield) as a colorless oil: $[α]_D$ +25.5° (c 1.0, CHCl$_3$); $^1$H NMR (400 MHz, CDCl$_3$) δ

3.99 (1H, d, J=2.1 Hz, 8α-H), 3.64 (2H, t, J=6.6 Hz, CH$_2$OH), 1.92 (1H, dm, J=12.3 Hz), 0.907 (3H, s, 18-H$_3$), 0.886 (9H, s, Si-t-Bu), 0.81 (3H, d, J=6.6 Hz, 21-H$_3$), 0.007 and −0.006 (each, 3H, each s, SiMe$_2$); $^{13}$C NMR (100 MHz) δ 69.43 (d, C-8), 63.18 (t, C-25), 56.31 (d), 53.10 (d), 42.17 (s, C-13), 40.65 (t), 35.05 (t), 34.70 (d), 34.45 (t), 33.20 (t), 27.17 (t), 25.79 (q, SiCMe$_3$), 22.94 (t), 22.35 (t), 18.53 (q, C-21), 18.02 (s, SiCMe$_3$), 17.71 (t), 14.03 (q, C-18), −4.81 and −5.17 (each q, each SiMe); MS (EI) m/z no M$^+$, 325 (3, M$^+$−C$_3$H$_7$), 311 (9, M$^+$−C$_4$H$_9$), 269 (6, M$^+$−C$_6$H$_{11}$O) 251 (16, M$^+$−H−t-BuSiMe$_2$H), 235 (25, M$^+$−H−t-BuSiMe$_2$OH), 219 (29), 163 (46), 135 (78), 109 (62), 75 (100); exact mass calculated for C$_{18}$H$_{35}$O$_2$Si (M$^+$−C$_4$H$_9$) 311.2406, found 311.2397.

Preparation of (20S)-de-A,B-8β-(tert-butyldimethylsilyl) oxy-20-butyl-pregnane (8)

To a stirred solution of the alcohol 7 (95 mg, 0.26 mmol), 4-dimethylaminopyridine (5 mg, 0.04 mmol) and triethylamine (145 μL, 105 mg, 1.04 mmol) in anhydrous methylene chloride (5 mL) p-toluenesulfonyl chloride (68 mg, 0.36 mmol) was added at 0° C. A cooling bath was removed and stirring was continued for 22 h. Methylene chloride (20 mL) was added and the mixture washed with a saturated aq. NaHCO$_3$ solution, dried (Na$_2$SO$_4$) and concentrated under reduced pressure. A residue was dissolved in anhydrous THF (5 mL) and lithium aluminium hydride (32 mg, 0.84 mmol) was added to the solution at 0° C. A cooling bath was removed and the mixture was stirred for 18 h at room temperature. The excess hydride was quenched by careful, successive addition of sat. aq. NH$_4$Cl. Methylene chloride (15 mL) and Celite (0.5 g) were added and the slurry was stirred for 20 min. The aluminium salts were separated by vacuum filtering the slurry through a Celite pad. The salts were repeatedly washed with methylene chloride. The filtrate was dried (Na$_2$SO$_4$) and concentrated under reduced pressure. A residue was chromatographed on silica gel with hexane/ethyl acetate (97:3) to give the product 8 (85 mg, 93% yield): [α]$_D$ +25.3° (c 1.26, CHCl$_3$); $^1$H NMR (400 MHz, CDCl$_3$) δ 4.00 (1H, d, J=2.1 Hz, 8α-H), 1.95 (1H, dm, J=12.4 Hz), 0.914 (3H, s, 18-H$_3$), 0.893 (9H, s, Si-t-Bu), 0.81 (3H, d, J=6.6 Hz, 21-H$_3$), 0.013 and 0.000 (each 3H, each s, each SiMe); $^{13}$C NMR (100 MHz) δ 69.52 (d, C-8), 56.47 (d), 53.15 (d), 42.19 (s, C-13), 40.68 (t), 35.02 (t), 34.79 (d), 34.52 (t), 28.56 (t), 27.21 (t), 25.81 (q, SiMe$_3$), 23.09 (t), 22.99 (t), 18.62 (q, C-21), 18.05 (s, SiCMe$_3$), 17.75 (t), 14.26 (q, C-25), 14.02 (q, C-18), −4.79 and −5.16 (each q, each SiMe); MS (EI) m/z 352 (2, M$^+$), 337 (4, M$^+$−CH$_3$), 295 (81, M$^+$−t-Bu), 253 (13, M$^+$−C$_6$H$_{11}$O), 219 (71, M$^+$−H−t-BuSiMe$_2$OH), 177 (10), 135 (22), 75 (100); exact mass calculated for C$_{18}$H$_{35}$OSi (M$^+$−C$_4$H$_9$) 295.2457, found 295.2454.

Preparation of (20S)-de-A,B-20-butyl-pregnan-8β-ol (9)

The protected alcohol 8 (84 mg, 0.24 mmol) was dissolved in anhydrous THF (5 mL) and anhydrous methanol (5 mL). Hydrogen fluoride-pyridine complex (4 mL) was added followed at room temperature and the mixture was sired for 19 h. Ethyl acetate (20 mL) was added and the organic phase washed with brine and water, dried (Na$_2$SO$_4$) and concentrated under reduced pressure. The residue was diluted with hexane and chromatographed on silica gel with hexane to give the product 9 (17 mg, 30% yield) as a colorless oil: $^1$H NMR (500 MHz, CDCl$_3$) δ 4.07 (1H, d, J=2.5 Hz, 8α-H), 1.98 (1H, dm, J=13.1 Hz), 1.88-1.76 (3H, m), 0.927 (3H, s, 18-H$_3$), 0.89 (3H, t, J=7.1 Hz, 25-H$_3$), 0.81 (3H, d, J=6.6 Hz, 21-H$_3$); $^{13}$C NMR (125 MHz) δ 69.46 (d, C-8), 56.32 (d), 52.67 (d), 41.90 (s, C-13), 40.32 (t), 34.97 (t), 34.76 (d), 33.59 (t), 28.52 (t), 27.05 (t), 23.08 (t), 22.42 (t), 18.56 (q, C-21), 17.49 (t), 14.23 (q, C-25), 13.77 (q, C-18).

Preparation of (20S)-de-A,B-20-butyl-pregnan-8-one (II)

Pyridinium dichromate (118 mg, 314 μmol) was added to a solution of the alcohol 9 (15 mg, 63 μmol) and pyridinium p-toluenesulfonate (2 mg, 8 μmol) in anhydrous methylene chloride (5 mL). The resulting suspension was stirred at room temperature for 2 h. The reaction mixture was filtered through a Waters silica Sep-Pak cartridge (5 g) that was further washed with hexane/ethyl acetate (95:5). After removal of solvents the ketone II (12 mg, 81% yield) was obtained as a colorless oil: $^1$H NMR (400 MHz, CDCl$_3$) δ 2.45 (1H, dd, J=11.5, 7.6 Hz), 2.32-2.16 (2H, m), 0.90 (3H, t, J=6.9 Hz, 25-H$_3$), 0.85 (3H, d, J=6.1 Hz, 21-H$_3$), 0.634 (3H, s, 18-H$_3$); $^{13}$C NMR (100 MHz) δ 212.14 (C-8), 62.01 (C-14), 56.24, 49.96 (C-13), 40.96, 38.86, 35.18, 34.87, 28.43, 27.15, 24.06, 23.03, 18.94 (C-21), 18.51, 14.19 (C-25), 12.72 (C-18).

Preparation of (20S)-2-methylene-19,26,27-trinor-1α-hydroxycalciferol (I).

To a solution of phosphine oxide 11 (60 mg, 103 μmol) in anhydrous THF (600 μL) at −20° C. was slowly added PhLi (1.8 M in cyclohexane-ether, 60 μL, 108 μmol) under argon with stirring. The solution turned deep orange. After 30 min the mixture was cooled to −78° C. and a precooled (−78° C.) solution of ketone II (12 mg, 51 μmol) in anhydrous THF (200 μL) was slowly added. The mixture was stirred under argon at −78° C. for 3 h and at 0° C. for 18 h. Ethyl acetate was added, and the organic phase was washed with brine, dried (Na$_2$SO$_4$) and evaporated. The residue was dissolved in hexane and applied on a Waters silica Sep-Pak cartridge (2 g). The cartridge washed with hexane and hexane/ethyl acetate (99.5: 0.5) to give 19-norvitamin derivative 12 (13 mg). The Sep-Pak was then washed with hexane/ethyl acetate (96:4) to recover the unchanged C,D-ring ketone II (6 mg, 25 μmol), and with ethyl acetate to recover diphenylphosphine oxide 11 (56 mg). The protected vitamin 12 was further purified by HPLC (9.4×250 mm Zorbax-Silica column, 4 mL/min) using hexane/2-propanol (99.9:0.1) solvent system. Pure compound 12 (8.3 mg, 53% yield) was eluted at R$_f$=3.2 min as a colorless oil: MS (EI) m/z 600 (14, M$^+$), 585 (4, M$^+$−Me), 543 (11, M$^+$−C$_4$H$_9$), 468 (100, M$^+$−t-BuMe$_2$SiOH), 366 (43), 323 (9), 257 (13), 234 (16), 147 (24), 73 (97); exact mass calculated for C$_{37}$H$_{68}$O$_2$Si$_2$ (M$^+$) 600.4758, found 600.4742.

Protected vitamin 12 (8 mg, 13 μmol) was dissolved in anhydrous THF (4 mL) and a solution of tetrabutylammonium fluoride (1 M in THF, 100 μL, 100 μmol) was added, followed by freshly activated molecular sieves 4A (300 mg). The mixture was stirred under argon at room temperature for 4 h, then diluted with 2 mL of hexane/ethyl acetate (9:1) and applied on a Waters silica Sep-Pak cartridge (2 g). Elution with the same solvent system gave the crude product I that was further purified by HPLC (9.4×250 mm Zorbax-Silica column, 4 mL/min) using hexane/2-propanol (9:1) solvent system. Analytically pure 2-methylene-19-norvitamin I (3.59 mg, 74% yield) was collected at R$_f$=6.4 min. as a colorless oil: UV (in EtOH) λ$_{max}$ 261, 251, 243 nm; $^1$H NMR (750 MHz, CDCl$_3$) δ 6.36 and 5.89 (1H and 1H, each d, J=11.2 Hz, 6- and 7-H), 5.11 and 5.09 (each 1H, each s, =CH$_2$), 4.47 (2H, m, 1β- and 30α-H), 2.84 (1H, dd, J=13.3, 4.4 Hz, 10β-H), 2.82 (1H, br d, J=12.3 Hz, 9β-H), 2.58 (1H, dd, J=13.3, 3.4 Hz, 4α-H), 2.32 (1H, dd, J=13.3, 6.1 Hz, 4β-H), 2.30 (1H, dd, J=13.3, 8.4 Hz, 10α-H), 2.05-1.95 (2H, m), 1.90-1.82 (1H, m), 0.89 (3H, t, J=7.1 Hz, 25-H$_3$), 0.84 (3H, d, J=6.5 Hz, 21-H$_3$), 0.552 (3H, s, 18-H$_3$); $^{13}$C NMR (100 MHz) δ 151.97 (s, C-2), 143.55 (s, C-8), 130.29 (s, C-5), 124.30 (d, C-6), 115.24 (d, C-7), 107.71 (t, =CH$_2$), 71.82 and 70.70 (each d, C-1 and C-3), 56.36 (d), 56.22 (d), 45.84 (s, C-13), 45.79 (t), 40.34 (t), 38.16 (t), 35.45 (d), 35.29 (t), 28.98 (t), 28.55 (t),

27.29 (t), 23.51 (t), 23.08 (t), 22.17 (t), 18.59 (q, C-21), 14.23 (q, C-25), 12.33 (q, C-18); MS (EI) m/z 372 (100, M$^+$), 354 (4, M$^+$−H$_2$O), 324 (15, M$^+$−H$_2$O−C$_2$H$_6$), 287 (60, M$^+$−C$_6$H$_{13}$), 269 (22, M$^+$−C$_6$H$_{13}$−H$_2$O), 251 (18, M$^+$−C$_6$H$_{13}$−2H$_2$O), 231 (22), 219 (35), 147 (46), 135(76), 119 (27), 107 (61); exact mass calculated for C$_{25}$H$_{40}$O$_2$ (M$^+$) 372.3028 found 372.3039.

Scheme 2

Scheme 3

-continued

I

Figure 1:
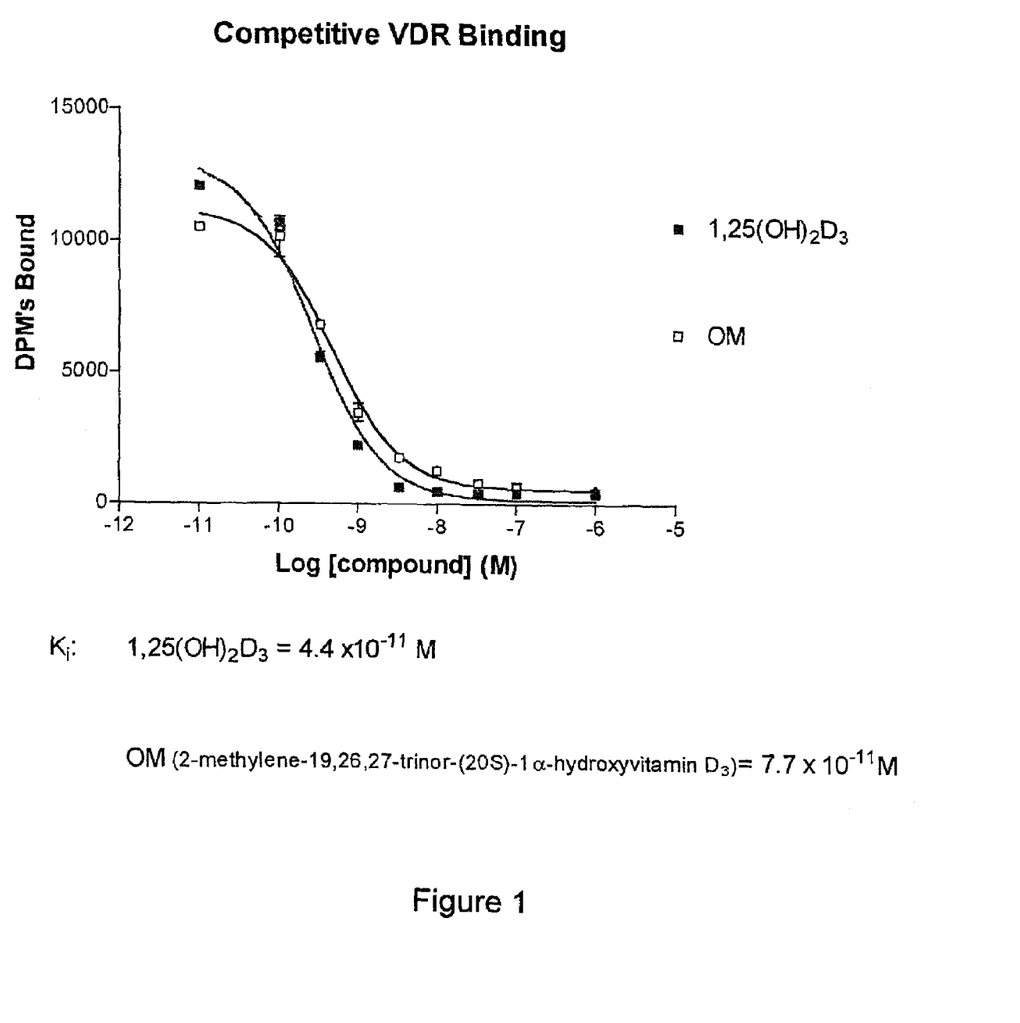
FIG. 1 is a graph illustrating the relative activity of OM and $1,25(OH)_2D_3$ to compete for binding with [$^3$H]-1,25-$(OH)_2$-$D_3$ to the full-length recombinant rat vitamin D receptor.

Biological Activity of 2-Methylene-19,26,27-Trinor-(20S)-1α-Hydroxyvitamin $D_3$ The introduction of a methylene group to the 2-position and the removal of the two methyl groups at the 26 and 27 positions in the side chain of 1α-hydroxy-19-nor-(20S)-vitamin $D_3$ had little or no effect on binding to the full length recombinant rat vitamin D receptor, as compared to 1α,25-dihydroxyvitamin $D_3$. The compound OM bound equally well to the receptor as compared to the standard 1,25-$(OH)_2D_3$ (FIG. 1). It might be expected from these results that compound OM would have equivalent biological activity. Surprisingly, however, compound OM is a highly selective analog with unique biological activity.

Figure 6:
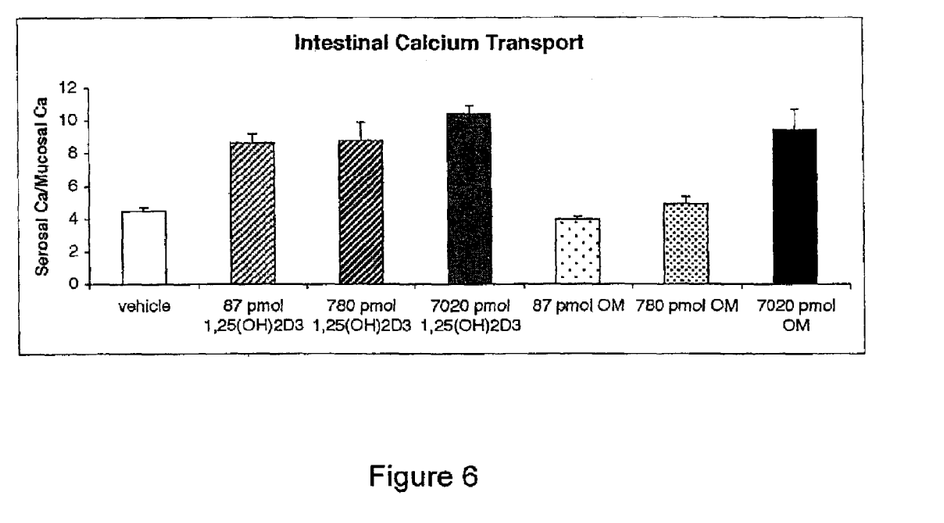
FIG. 6 is a bar graph illustrating the intestinal calcium transport activity of $1,25(OH)_2D_3$ as compared to OM.

FIG. 6 shows that OM has very little activity as compared to that of 1,25-dihydroxyvitamin $D_3$ (1,25$(OH)_2D_3$), the natural hormone, in stimulating intestinal calcium transport.

Figure 4:
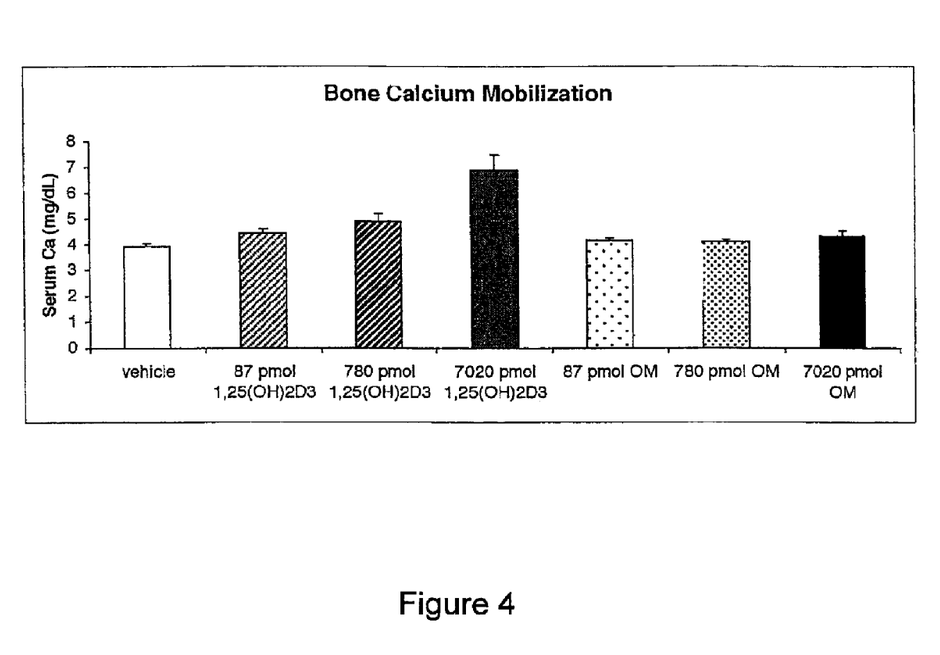
FIGS. 4 and 5 are bar graphs illustrating the bone calcium mobilization activity of $1,25(OH)_2D_3$ as compared to OM. Each graph represents a separate batch of vitamin D-deficient animals. The results depicted in FIG. 5 are not vehicle-controlled, but rather each animal serves as its own control because the animals were bled pre- and post-dose.
Figure 5:
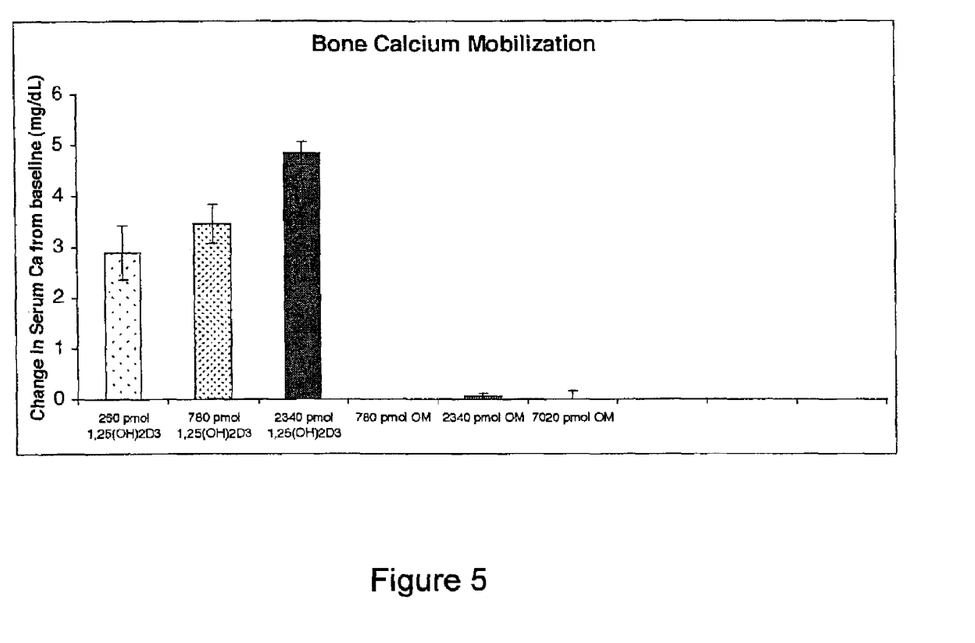

FIGS. 4 and 5 demonstrate that OM has very little bone calcium mobilization activity, as compared to 1,25$(OH)_2D_3$.

FIGS. 4-6 thus illustrate that OM may be characterized as having little, if any, calcemic activity.

Figure 2:
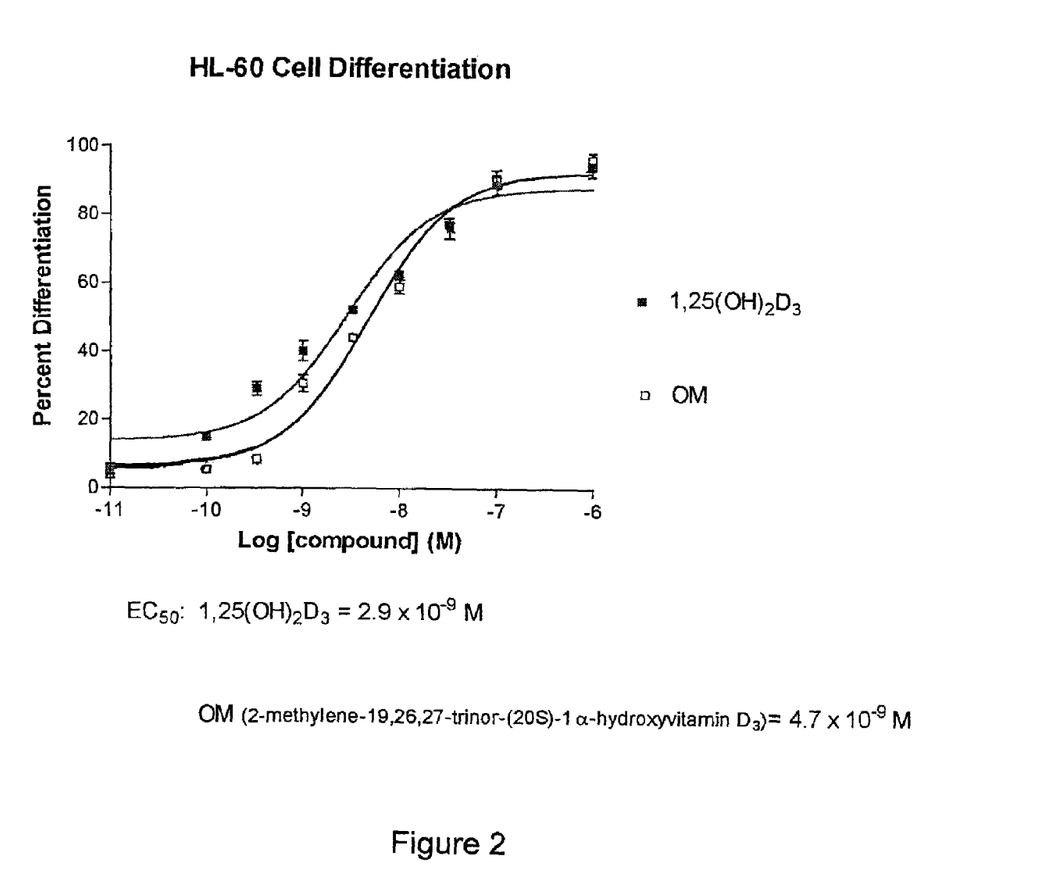
FIG. 2 is a graph illustrating the percent HL-60 cell differentiation as a function of the concentration of OM and $1,25(OH)_2D_3$.

FIG. 2 illustrates that OM is almost as potent as 1,25$(OH)_2D_3$ on HL-60 cell differentiation, making it an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
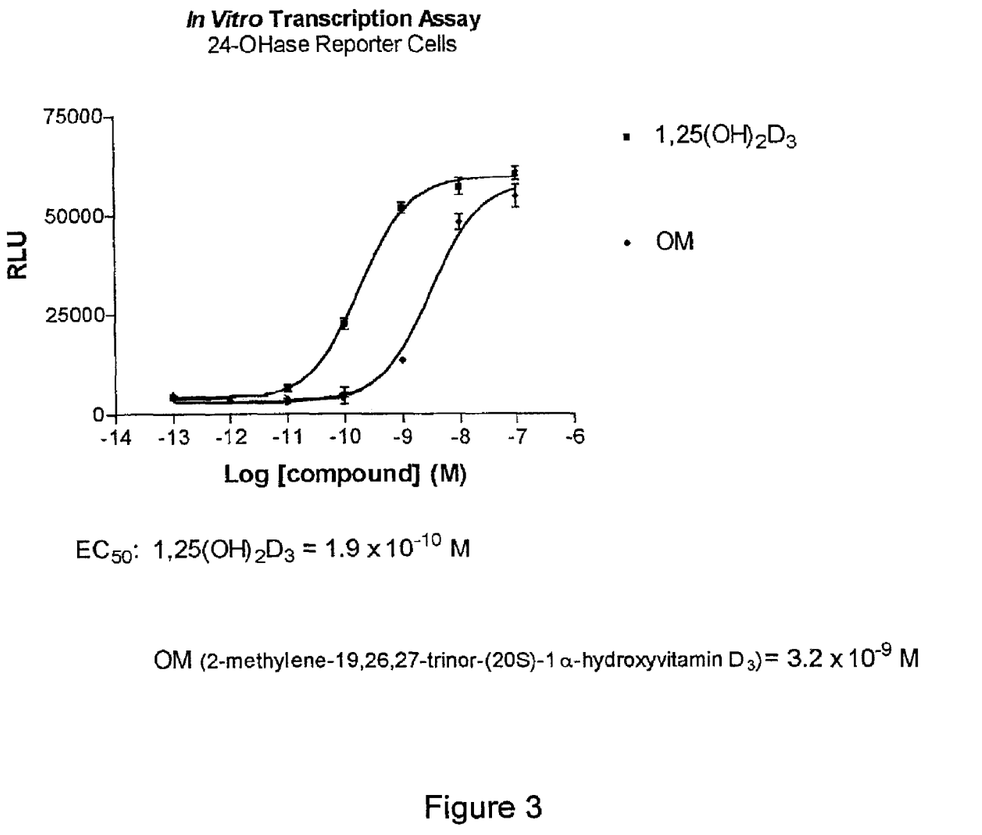
FIG. 3 is a bar graph illustrating the in vitro transcription activity of $1,25(OH)_2D_3$ as compared to OM.

FIG. 3 illustrates that the compound OM has transcriptional activity in bone cells, but less than 1α,25-dihydroxyvitamin $D_3$. This result, together with the cell differentiation activity of FIG. 2, suggests that OM will be very effective in psoriasis because it has direct cellular activity in causing cell differentiation and in suppressing cell growth. These data also indicate that OM may have significant activity as an anti-cancer agent, especially against leukemia, colon cancer, breast cancer, skin cancer and prostate cancer. The strong activity of OM on HL-60 differentiation suggests it will be active in suppressing growth of parathyroid glands and in the suppression of the preproparathyroid gene.

Experimental Methods

Vitamin D Receptor Binding
Test Material

Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25 $(OH)_2D_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25$(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation
Test Material

Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2\times10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca) diet +AEK for one week followed by Diet 11 (0.02% Ca) +AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

VDR binding, HL60 cell differentiation, and transcription activity. OM ($K_i=7.7\times10^{-11}$M) is nearly equivalent to the natural hormone 1α,25-dihydroxyvitamin $D_3$ ($K_i=4.4\times10^{11}$M) in its ability to compete with [$^3$H]-1,25(OH)$_2$D$_3$ for binding to the full-length recombinant rat vitamin D receptor (FIG. 1). There is also little difference between OM ($EC_{50}=4.7\times10^{-9}$M) in its ability (efficacy or potency) to promote HL60 differentiation as compared to 1α,25-dihydroxyvitamin $D_3$ ($EC_{50}=2.9\times10^{-9}$M) (See FIG. 2). Compound OM ($EC_{50}=3.2\times10^{-9}$M) has transcriptional activity in bone cells but less than 1α,25-dihydroxyvitamin $D_3$ ($EC_{50}=1.9\times10^{-10}$M) (See FIG. 3). These results suggest that OM will be very effective in psoriasis because it has direct cellular activity in causing cell differentiation and in suppressing cell growth. These data also indicate that OM will have significant activity as an anti-cancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism.

Calcium mobilization from bone and intestinal calcium absorption in vitamin D-deficient animals. Using vitamin D-deficient rats on a low calcium diet (0.02%), the activities of OM and 1,25(OH)$_2$D$_3$ in intestine and bone were tested. As expected, the native hormone (1,25(OH)$_2$D$_3$) increased serum calcium levels at all dosages (FIG. 4). FIG. 4 and FIG. 5 show that OM has little, if any, activity in mobilizing calcium from bone. Administration of OM at 87 pmol/day for 4 consecutive days did not result in mobilization of bone calcium, and increasing the amount of OM to 780 pmol/day and then to 7020 pmol/day was also without any substantial effect.

Intestinal calcium transport was evaluated in the same groups of animals using the everted gut sac method (FIG. 6). These results show that the compound OM does not promote intestinal calcium transport when administered at either 87 or 780 pmol/day, whereas 1,25(OH)$_2$D$_3$ promotes a significant increase at the 87 and 780 pmol/day doses. It was only when 7020 pmol/day of OM was administered that significant intestinal calcium transport activity was recorded, an almost 10-fold increase in dosage over the 780 pmol/day dose. Thus, it may be concluded that OM is essentially devoid of intestinal calcium transport activity at the recommended lower doses.

These results illustrate that OM is an excellent candidate for numerous human therapies as described herein, and that it may be particularly useful in a number of circumstances such as suppression of secondary hyperparathyroidism of renal osteodystrophy, autoimmune diseases, cancer, and psoriasis. OM is an excellent candidate for treating psoriasis because: (1) it has significant VDR binding, transcription activity and cellular differentiation activity; (2) it is devoid of hypercalcemic liability unlike 1,25(OH)$_2$D$_3$; and (3) it is easily synthesized. Since OM has significant binding activity to the vitamin D receptor, but has little ability to raise blood serum calcium, it may also be particularly useful for the treatment of secondary hyperparathyroidism of renal osteodystrophy.

These data also indicate that the compound OM of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound OM of the invention.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I, and particularly OM, may be administered orally, topically, parenterally, rectally, nasally, sublingually or transdermally. The compounds may be advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 μg to 1000 μg per day of the compounds I, and particularly compound OM, preferably from about 0.1 μg to about 500 μg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds, particularly the compound OM as defined by the above formula I and Ia as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually or parenterally in dosages of from about 0.01 μg/day to about 1000 μg/day, and preferably from about 0.1 μg/day to about 500 μg/day.

The compounds I, and particularly compound OM may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, and particularly compound OM is advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

What is claimed is:

1. A method of treating obesity of an animal, inhibiting adipoctye differentiation, inhibiting SCD-1 gene transcription, and/or reducing body fat in an animal comprising administering to an animal in need thereof an effective amount of a compound having the formula:

where $X_1$ and $X_2$, which may be the same or different, are each selected from hydrogen or a hydroxy-protecting group.

2. The method of claim 1 wherein the compound is administered orally.

3. The method of claim 1 wherein the compound is administered parenterally.

4. The method of claim 1 wherein the compound is administered transdermally.

5. The method of claim 1 wherein the compound is administered rectally.

6. The method of claim 1 wherein the compound is administered nasally.

7. The method of claim 1 wherein the compound is administered sublingually.

8. The method of claim 1 wherein the compound is administered in a dosage of from about 0.01 μg/day to about 1000 μg/day.

9. The method of claim 1 wherein the compound is 2-methylene-19,26,27-trinor-(20S)-1α-hydroxyvitamin $D_3$ having the formula:

10. The method of claim 1 wherein the animal is a human.

11. The method of claim 1 wherein the animal is a domestic animal.

12. The method of claim 1 wherein the animal is an agricultural animal.

13. A method of treating acne in an animal, the method comprising administering to an animal in need thereof an effective amount of a compound having the formula:

where $X_1$ and $X_2$, which may be the same or different, are each selected from hydrogen or a hydroxy-protecting group.

14. The method of claim 13 wherein the compound is administered orally.

15. The method of claim 13 wherein the compound is administered parenterally.

16. The method of claim 13 wherein the compound is administered transdermally.

17. The method of claim 13 wherein the compound is administered rectally.

18. The method of claim 13 wherein the compound is administered nasally.

19. The method of claim 13 wherein the compound is administered sublingually.

20. The method of claim 13 wherein the compound is administered in a dosage of from about 0.01 μg/day to about 1000 μg/day.

21. The method of claim 13 wherein the compound is 2-methylene-19,26,27-trinor-(20S)-1α-hydroxyvitamin $D_3$ having the formula:

22. A method of treating hypertension in an animal, the method comprising administering to an animal in need thereof an effective amount of a compound having the formula:

where $X_1$ and $X_2$, which may be the same or different, are each selected from hydrogen or a hydroxy-protecting group.

23. The method of claim 22 wherein the compound is administered orally.

24. The method of claim 22 wherein the compound is administered parenterally.

25. The method of claim 22 wherein the compound is administered transdermally.

26. The method of claim 22 wherein the compound is administered rectally.

27. The method of claim 22 wherein the compound is administered nasally.

28. The method of claim 22 wherein the compound is administered sublingually.

29. The method of claim 22 wherein the compound is administered in a dosage of from about 0.01 μg/day to about 1000 μg/day.

30. The method of claim 22 wherein the compound is 2-methylene-19,26,27-trinor-(20S)-1α-hydroxyvitamin $D_3$ having the formula:

* * * * *